United States Patent [19]
Berndt

[11] Patent Number: 6,074,870
[45] Date of Patent: Jun. 13, 2000

[54] OPTICAL BLOOD CULTURE SENSOR

[75] Inventor: Klaus W. Berndt, Stewartstown, Pa.

[73] Assignee: Becton, Dickinson and Company, Franklin Lakes, N.J.

[21] Appl. No.: 08/290,405

[22] Filed: Aug. 15, 1994

[51] Int. Cl.[7] .................................................. C12M 1/34
[52] U.S. Cl. ................... 435/287.5; 435/288.7; 435/34
[58] Field of Search ................... 435/29, 31, 34, 435/287.5, 288.7, 808; 422/82.06, 82.07, 82.08; 250/459.1, 461.1, 461.2

[56] References Cited

U.S. PATENT DOCUMENTS 4,791,310  12/1988  Honig et al. .
4,945,060   7/1990  Turner et al. .
5,372,784  12/1994  Morris et al. .
5,372,936  12/1994  Fraatz et al. .

FOREIGN PATENT DOCUMENTS 0 105 870  4/1984  European Pat. Off. .
2 132 348  7/1984  United Kingdom .

*Primary Examiner*—William H. Beisner
*Attorney, Agent, or Firm*—Alan W Fiedler

[57] ABSTRACT

A culture medium and blood specimen are introduced into a sealable glass vial having a head space gas mixture such that a change in the gas mixture composition can be monitored by a chemically sensitive material in the vial comprising a mixture of two fluorescent sensor materials. The first sensor material exhibits a long fluorescence decay time and/or a fluorescence intensity that depend on a first chemical parameter, such as oxygen concentration. The second sensor material exhibits a fluorescence intensity that depends on a second chemical parameter, such as pH or carbon dioxide concentration, the fluorescence decay time of the second sensor material being extremely short.

44 Claims, 16 Drawing Sheets

OPTICAL BLOOD CULTURE SENSOR

BACKGROUND OF THE INVENTION

The present invention relates to a non-invasive method and apparatus for detecting biological activities in a fluid specimen, such as blood, urine or sputum, where the specimen and a culture medium are introduced into sealable containers and are exposed to conditions enabling a variety of metabolic, physical, and chemical changes to take place in the presence of microorganisms in the sample. The biological activity being detected by a variety of chemical sensors that are based on changes in fluorescence lifetime and/or intensity.

Usually, the presence of microorganisms such as bacteria in a patient's body fluid, particularly blood, is determined using blood culture vials. A small quantity of blood is injected through a sealing rubber septum into a sterile vial containing a culture medium. The vial is incubated at a temperature conducive to bacterial growth, e.g., 37° C., and monitored for such growth.

Common visual inspection involves monitoring the turbidity of the liquid suspension. Known instrumental methods detect changes in the $CO_2$ content in the head space of the culture bottles, which is a metabolic by-product of the bacterial growth. Monitoring the $CO_2$ content can be accomplished by conventional methods, including radiochemical, infrared absorption at a $CO_2$ spectral line, or pressure/vacuum measurement. These methods, however, require invasive procedures which can result in cross-contamination between vials.

Recently, novel non-invasive methods have been developed which use chemical sensors inside a vial. Such sensors often respond to changes in the $CO_2$ concentration by changing their color or by changing their fluorescence intensity (see, e.g., U.S. Pat. No. 4,945,060). The outputs from these sensors are based upon light intensity measurements. This means that errors may occur, particularly if the light sources used to excite the sensors, or the photodetectors used to monitor intensities, exhibit aging effects over time.

In known automated non-invasive blood culture systems, individual light sources, individual spectral excitation and emission filters, and individual photodetectors are arranged adjacent to each vial. Such arrangements result in certain station sensitivity variations from one vial to the next. Due to the fact that most known blood culture sensors generate only a moderate contrast ratio in the measured photocurrent during bacterial growth, extensive and time-consuming calibration procedures and sophisticated detection algorithms are required to operate these systems. Moreover, light sources, spectral filters, and photodetectors with extreme narrow specification tolerances must be utilized.

Even if it would be possible to equalize all vial stations, certain variations in the vial shape would still remain and affect the measured fluorescence photocurrent. In fluorescence intensity-based sensor arrangements, any drift in the excitation source intensity, any change in the photodetector sensitivity, or any dust contamination on an optical surface will also cause a change in the measured photocurrent. Therefore, the long-time stability of such an instrument would be poor and frequent re-calibration would be required.

The disadvantage of intensity-based sensor arrangements can be overcome by utilizing fluorescent sensors that change their fluorescence lifetime, wherein intensity measurement is replaced with time parameter measurement and intensity changes have no impact on the sensor output signal. Many chemical sensor materials are known that change their fluorescence lifetime with changing oxygen concentration, pH, carbon dioxide concentration, or other chemical parameters (see, e.g., G.B. Patent No. 2,132,348).

A change in sensor fluorescence lifetime is commonly monitored by applying a well-known phase shift method (see, e.g., U.S. Pat. No. 5,030,420), wherein the excitation light is intensity-modulated. That method results in an intensity-modulated fluorescence emission that is phase-shifted relative to the excitation phase. Phase shift angle, $\theta$, being dependent on the fluorescence lifetime, $\tau$, according to the equation:

$$\tan \theta = \omega \tau \qquad (1)$$

where $\omega = 2\pi f$, is the circular light modulation frequency.

An inspection of equation (1) reveals that the phase shift method allows for maximum resolution, $d\theta/d\tau$, under the condition $\omega\tau = 1$. Unfortunately, almost all known pH- or carbon dioxide-sensitive fluorophores have decay times in the range 5 ns to 500 ps. In other words, light modulation frequencies, $f = \frac{1}{2}\pi\tau$, in the range 32 MHz to 320 MHz would be required.

It is possible to accomplish light intensity modulation at such high frequencies, however, this would require acousto-optic or electro-optic modulators which are only efficient in combination with lasers. Moreover, detecting the modulated fluorescence light would require highly sensitive high-speed photodetectors, such as micro channel-plate photomultipliers, which are rather expensive. Consequently, all commercial automated blood culture systems are based on intensity monitoring, and none utilize time-resolved fluorescent carbon dioxide sensors.

SUMMARY OF THE INVENTION

The present invention overcomes problems identified in the art by providing a method and apparatus for reliably and non-invasively detecting biological activities in blood culture vials using an optical blood culture sensor that is based on time-resolved fluorescence measurement that avoids the fluorescence intensity limitations discussed above.

According to the present invention, a culture medium and blood specimen are introduced into a sealable glass vial having a head space gas mixture such that a change in the gas mixture composition can be monitored by a chemically sensitive composite material in the vial. The chemically sensitive composite material comprises a mixture of two fluorescent sensor materials. The first sensor material exhibits a long fluorescence decay time and/or a fluorescence intensity that depend on a first chemical parameter, such as oxygen concentration. The second sensor material exhibits a fluorescence intensity that depends on a second chemical parameter, such as pH or carbon dioxide concentration, the fluorescence decay time of the second sensor material being at least one order of magnitude shorter than the fluorescence decay time of the first sensor material.

The first and second sensor materials are mixed into the same sensor matrix and are illuminated with intensity-modulated excitation light. The modulation frequency is chosen so that the condition $\omega\tau \approx 1$ holds for the first sensor material when the fluorescence lifetime has its minimum value. The fluorescence light emitted by the composite sensor is monitored using only one photodetector. The fluorescence photocurrent from the photodetector is split into its AC and DC components, that are measured separately. A sensor output signal is then generated by dividing the measured AC component by the measured DC component.

The present invention allows both sensor materials to operate in a time-resolved mode. Therefore, despite the extreme short decay time of the second sensor material, only one relatively low light modulation frequency is required. Therefore, a low-cost light emitting diode (LED) can be used as the excitation source. The time-resolved operational mode cancels out all drift effects due to light source aging, photodetector sensitivity changes, dust contamination on optical surfaces, and small deformations and/or displacements of the vials. The present invention therefore results in an extreme long-time stability for the automated blood culture instrument.

Changes in the sensor output signal can show the same or a different polarity for the two chemical parameters. If the long decay time of the first sensor material increases, then the AC/DC ratio decreases. If, e.g., the intensity of the second sensor material increases during bacterial growth, then the AC/DC ratio increases again. Therefore, changes regarding the two chemical parameters can be identified. In addition, in such a blood culture system, information can be obtained regarding the degree, the speed, and the relative time delay between oxygen consumption and carbon dioxide production. This information can then be used for partial identification of the growing microorganism.

According to the present invention, the mixture of the chemical sensor materials is disposed to the inner wall or to the inner bottom of the glass vial, and is illuminated by an excitation light source, preferably a blue LED. The LED is connected to an electronic signal source which provides a DC bias and a high-frequency modulation voltage. The signal source is equipped with a control input to allow for output power control that is connected to a computer.

Fluorescence light reemerging from the sensor material mixture is detected by means of a highly sensitive photodetector, such as a photomultiplier. An emission filter is arranged between the sensor material and the photodetector to reject back-scattered excitation light. The signal output of the photodetector is then fed to a first power splitter, one output of which is connected to the input of a first low-pass filter and then fed to the computer. The other output of the first power splitter is fed to the input of a first bandpass filter, the output of which is connected via a first high-frequency voltmeter to the computer. The computer is equipped with a data display unit.

Part of the excitation light emitted by the LED is coupled to the input of an optical fiber, and the output of the fiber is arranged in front of a photodiode that acts as a source monitor. The signal output of the source monitor photodiode is then fed to a second power splitter, one output of which is connected to the input of a second low-pass filter and then fed to the computer. The other output of the second power splitter is fed to the input of a second band-pass filter the output of which is connected via a second high-frequency voltmeter to the computer.

In operation, the light source illuminates the chemical sensor materials with intensity-modulated excitation light. By splitting the fluorescence photocurrent into its high-frequency and DC components, by measuring these components separately, and by calculating the ratio of the two components within the computer, a sensor output signal is generated that carries information regarding the response of the two sensor materials to different chemical parameters.

These and other features, objects, benefits and advantages of the present invention will become more apparent upon reading the following detailed description of the preferred embodiments, along with the appended claims in conjunction with the drawings, wherein reference numerals identify corresponding components.

DETAILED DESCRIPTION

Figure 1:
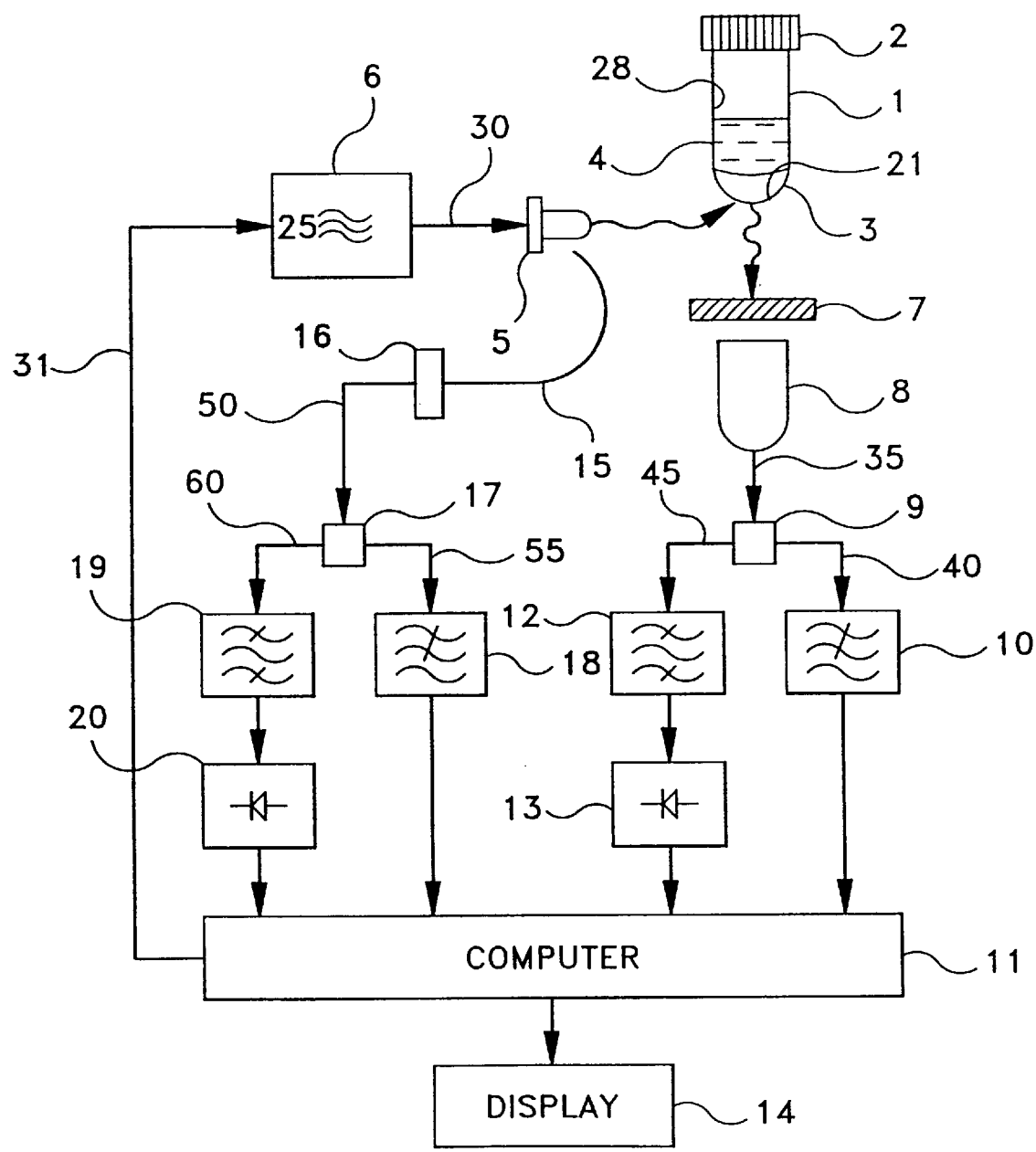
FIG. 1 shows schematically an optical blood culture sensor arrangement according to the present invention.

A preferred embodiment of a composite optical blood culture sensor arrangement embodying the principles and concepts of the invention is depicted schematically in FIG. 1. In this arrangement, a specimen and culture medium mixture 4 are introduced into an optically transparent container 1 that is sealed by a cap 2. A mixture of chemical sensor materials 3 is disposed to an inner wall 28 or an inner bottom surface 21 of container 1. The mixture 3 is illuminated by an excitation light source 5, preferably a blue LED, that is connected to an electronic signal source 6. Signal source 6 provides a DC bias and a high-frequency modulation voltage to light source 5 over a line 30, and is equipped with a power control input 25 connected by a line 31 to a computer 11.

Sensor material mixture 3 comprises a mixture of a first sensor material and a second sensor material, wherein the first sensor material exhibits a fluorescence decay time and/or a fluorescence intensity that depend on a first chemical parameter, such as oxygen concentration. The second sensor material, however, exhibits a fluorescence intensity that depends on a second chemical parameter, such as carbon dioxide concentration. The first sensor material can have a fluorescence decay time in the range 0.1 to 1000 $\mu$sec and even in the range 1 to 100 nsec, and the fluorescence decay time of the second sensor material is at least one order of magnitude shorter than the fluorescence decay time of the first sensor material. As a result, the invention allows both sensor materials to operate in a time-resolved mode and, despite the extreme short decay time of the second sensor material, only one relatively low light modulation frequency is required. Therefore, a low-cost LED can be used as light source 5. The time-resolved operational mode allows for cancellation of drift effects due to light source aging, photodetector sensitivity changes and small vial deformations and/or vial displacements.

Fluorescence light reemerging from sensor material mixture 3 is detected by a photodetector 8, e.g., a photomultiplier. An emission filter 7 is arranged between mixture 3 and photodetector 8 to prevent excitation light from light source 5 reaching photodetector 8. Photodetector 8 generates an output signal on a line 35 that is fed to a first power splitter 9. First power splitter 9 then generates two output signals, one of which is connected by a line 40 to the input of a first low-pass filter 10 that is connected directly to computer 11. The other output signal of first power splitter 9 is fed by a line 45 to the input of a first band-pass filter 12 that is connected via a first high-frequency voltmeter 13 to computer 11. Computer 11 is connected to a data display unit 14 to display information.

Part of the excitation light emitted by light source 5 is also coupled into the input of an optical fiber 15 that is arranged in front of a photodiode 16 that acts as a source monitor. Source monitor photodiode 16 then generates an output signal that is fed to a second power splitter 17 via a line 50. Second power splitter 17 then generates two output signals, one of which is connected by a line 55 to the input of a second low-pass filter 18 that is connected directly to computer 11. The other output signal of second power splitter 17 is fed by a line 60 to the input of a second band-pass filter 19 that is connected via a second high-frequency voltmeter 20 to computer 11.

In operation, light source 5 illuminates sensor material mixture 3 with excitation light that is intensity-modulated at a circular modulation frequency, $\omega$, having a modulation degree, m. The intensity modulation of the excitation light can be accomplished using different waveforms, but it is advantageous if the light source is periodically modulated. In particular, the excitation light can be sinusoidally modulated, square-wave modulated or periodically pulsed. The emitted fluorescence intensity of the first sensor material in mixture 3 can be described by:

$$F_1(t) = F_{01}\left[1 + \frac{m}{\sqrt{1+(\omega\tau)^2}}\right] * \sin[\omega t - \theta] \quad (2)$$

with $F_{01}$ being the average fluorescence intensity, and $$\theta = \arctan(\omega\tau) \quad (3)$$

being the fluorescence phase shift relative to the excitation modulation phase. The fluorescence lifetime, $\tau$, may depend on the time, t, according to the expression $$\tau(t) = k*h(t) \quad (4)$$

where k is a constant, and h(t) is a time-dependent function that rises from a first, lower level to a second, higher level as a consequence of oxygen consumption during microorganism growth.

Figure 2:
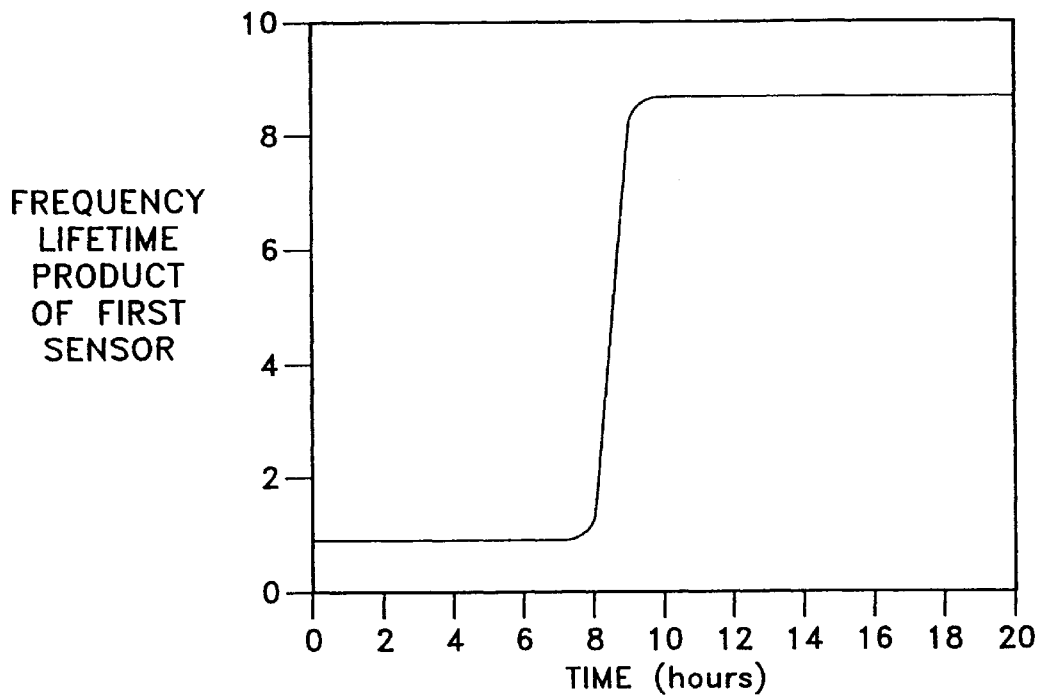
FIG. 2 is a plot showing frequency lifetime product, $\omega\tau$, versus time for the first sensor material in an aerobic vial.

Modulation frequency, $\omega$, is chosen so that the condition $\omega\tau \approx 1$ holds for the first sensor material when it has its minimum $\tau$-value. FIG. 2 depicts the frequency lifetime product, $\omega\tau$, versus time for the first sensor material in an aerobic vial.

The average fluorescence intensity, $F_{01}$, may also depend on the time, t, according to an expression $$F_{01}(t) = k'*h'(t) \quad (4A)$$

where k' is another constant, and h'(t) is another time-dependent function that also rises from a first, lower level to a second, higher level as a consequence of oxygen consumption during microorganism growth.

The fluorescence radiation emitted by the second sensor material in mixture 3 can be described by the equation $$F_2(t) = F_{02}[1 + m*\sin(t)] \quad (5)$$

with $F_{02}$ being the average fluorescence intensity of the second sensor material. In equation (5) it has been taken into account that the fluorescence decay time of the second sensor material is extremely short, so that the condition $\omega\tau << 1$ holds. Therefore, the fluorescence modulation degree is identical to the excitation modulation degree, m, and the fluorescence phase shift is so small that it can be neglected.

Figure 3:
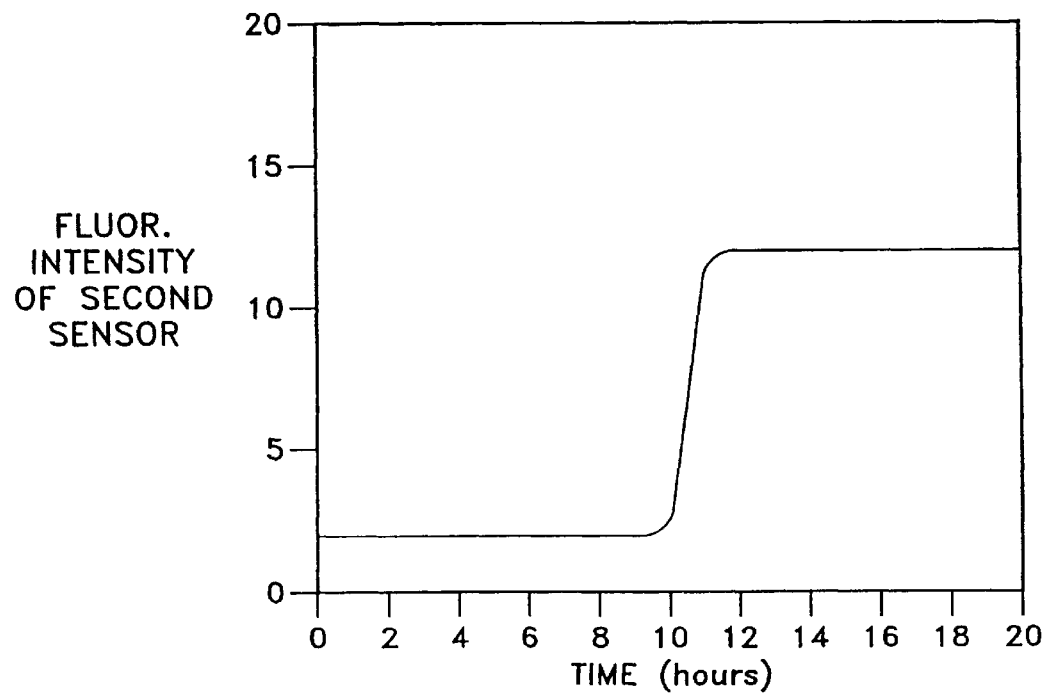
FIG. 3 is a plot showing fluorescence intensity versus time for the second sensor material for a strong carbon dioxide producing microorganism.

The average fluorescence intensity of the second sensor material, $F_{02}$, may depend on the time, t, according to the expression $$F_{02}(t)=c*g(t) \quad (6)$$

where c is a constant, and g(t) is a time-dependent function. The function g(t) can rise from a first, lower level to a second, higher level as a consequence of carbon dioxide production during microorganism growth. FIG. 3 depicts the average fluorescence intensity of the second sensor material versus time. In this case, the microorganism is a strong carbon dioxide producer. The function g(t) can also decrease from a first, higher level to a second, lower level, as discussed below.

In an optical blood culture sensor arrangement according to the present invention, the fluorescence photocurrent, I(t), is given by the expression $$I(t)=K(r,d,v)*[F_1(t)+F_2(t)] \quad (7)$$

where K(r,d,v) represents a function depending on the photodetector responsivity, r, the transmission, d, of different optical surfaces that show dust contamination effects, and on the exact vial shape, v.

The overall photocurrent I(t) is split into its AC and DC components, with each component being measured separately, and the AC/DC ratio is calculated within computer 11. Based on this, the following sensor output signal, AC/DC, is obtained $$\frac{AC}{DC} = \frac{\frac{mF_{01}(t)}{\sqrt{1+(\omega\tau(t))^2}}\sin[\omega t - \arctan(\omega\tau(t))] + F_{02}(t)m\sin(\omega t)}{F_{01}(t)+F_{02}(t)} \quad (8)$$

As can be seen from equation (8), the function K(r,d,v) is canceled out. Moreover, because the average fluorescence intensities $F_{01}(t)$ and $F_{02}(t)$ all are proportional to the excitation source intensity, aging effects of the LED are also canceled out. To avoid errors in the unlikely event that changes in modulation degree m occur, the sensor arrangement is provided with means to monitor and control the LED modulation. This is accomplished by means of the source monitor photodiode 16 and second power splitter 17.

Figure 4:
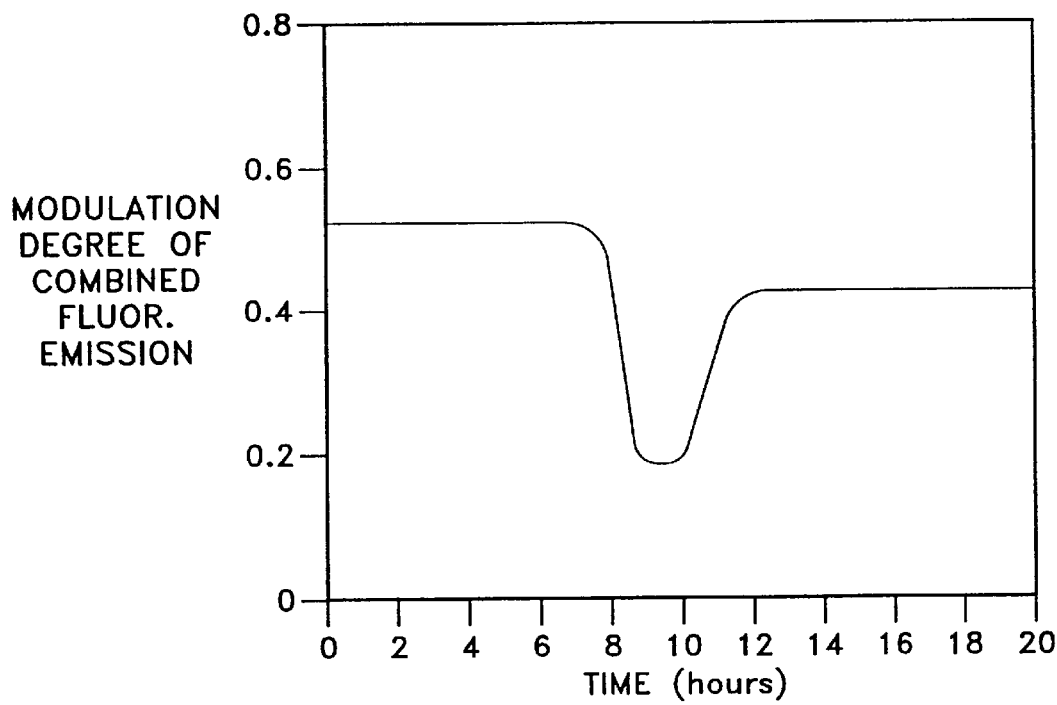
FIG. 4 is a plot showing modulation degree, AC/DC, of the combined fluorescence emission versus time, based on the individual sensor signals shown in FIGS. 2 and 3.
Figure 5:
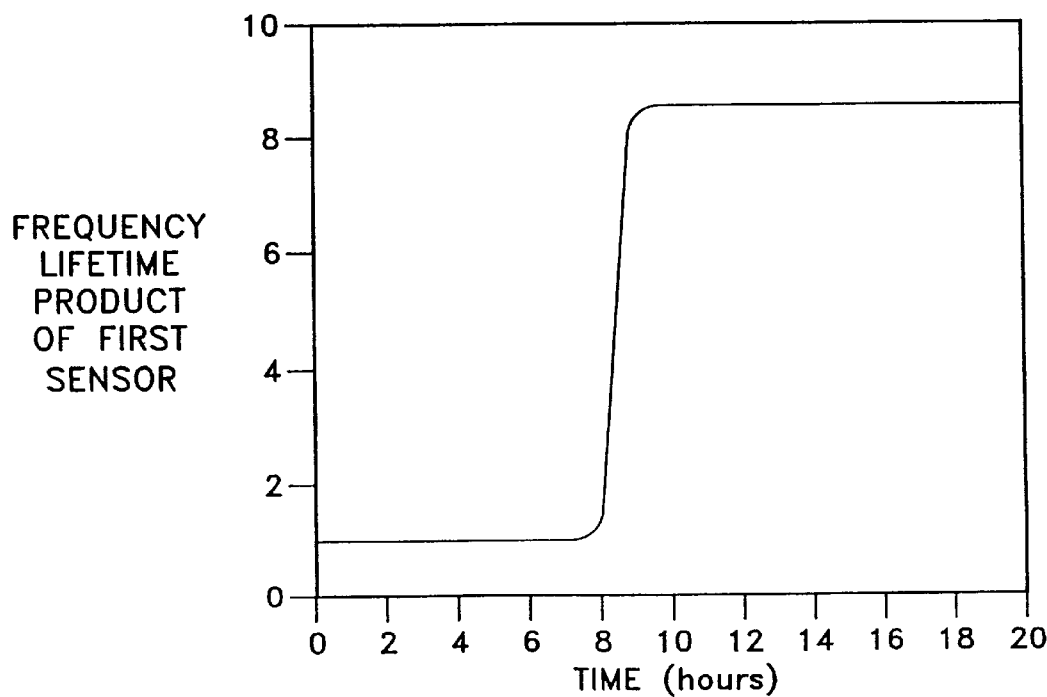
FIG. 5 is a plot showing frequency lifetime product, $\omega\tau$, versus time for the first sensor material in an aerobic vial.
Figure 6:
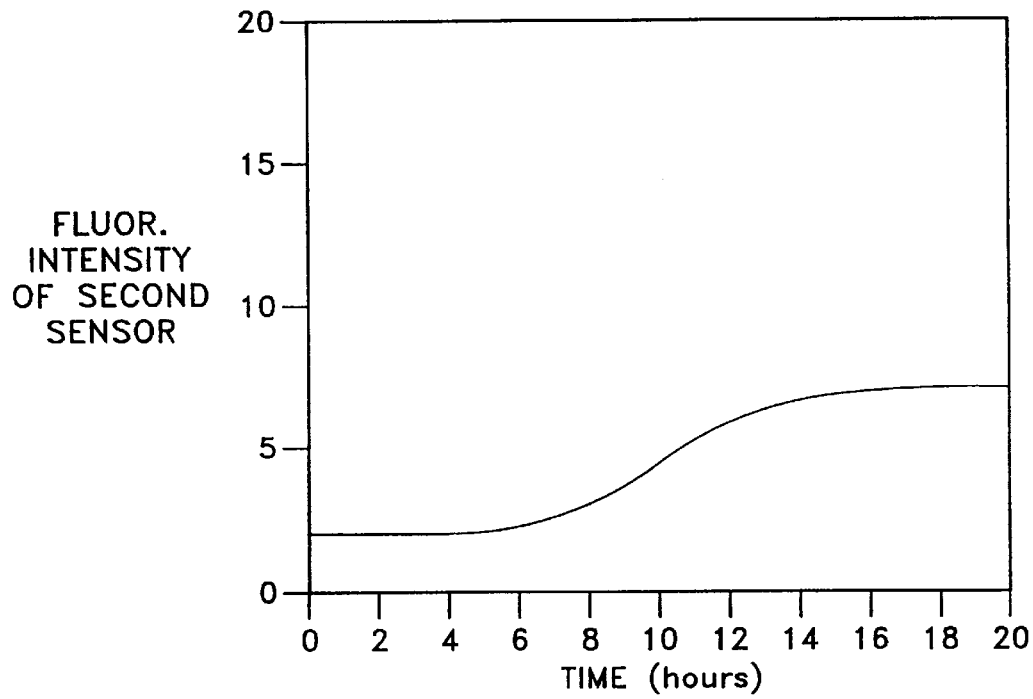
FIG. 6 is a plot showing fluorescence intensity versus time for the second sensor material for a weak carbon dioxide producing microorganism.
Figure 7:
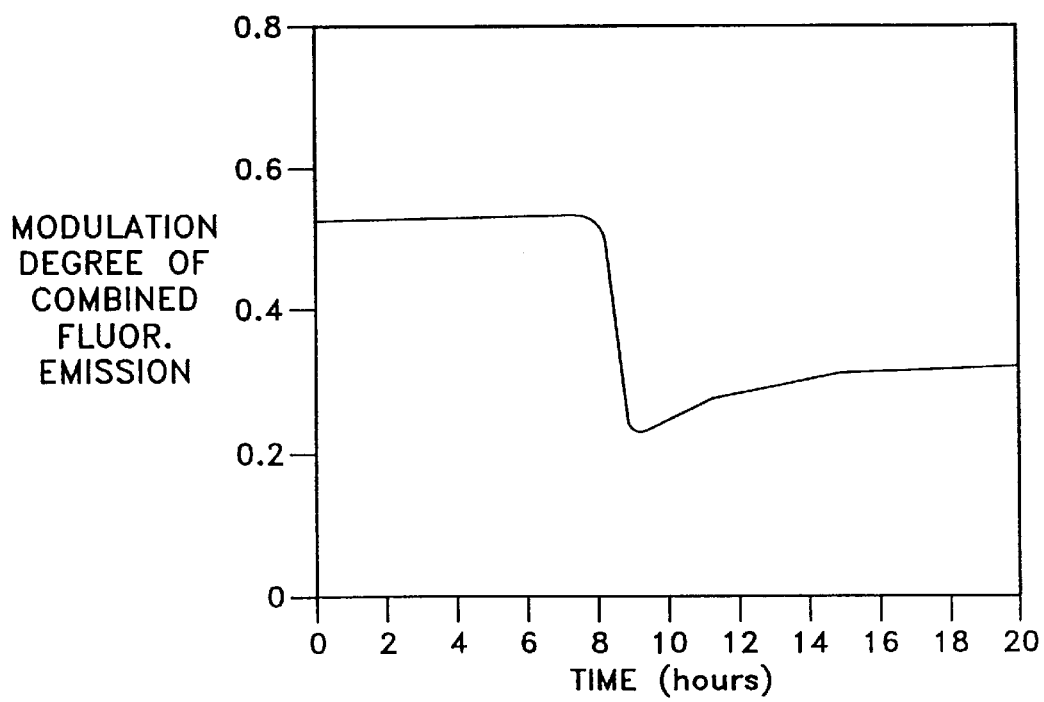
FIG. 7 is a plot showing modulation degree, AC/DC, of the combined fluorescent emission versus time, based on the individual sensor signals shown in FIGS. 5 and 6.
Figure 8:
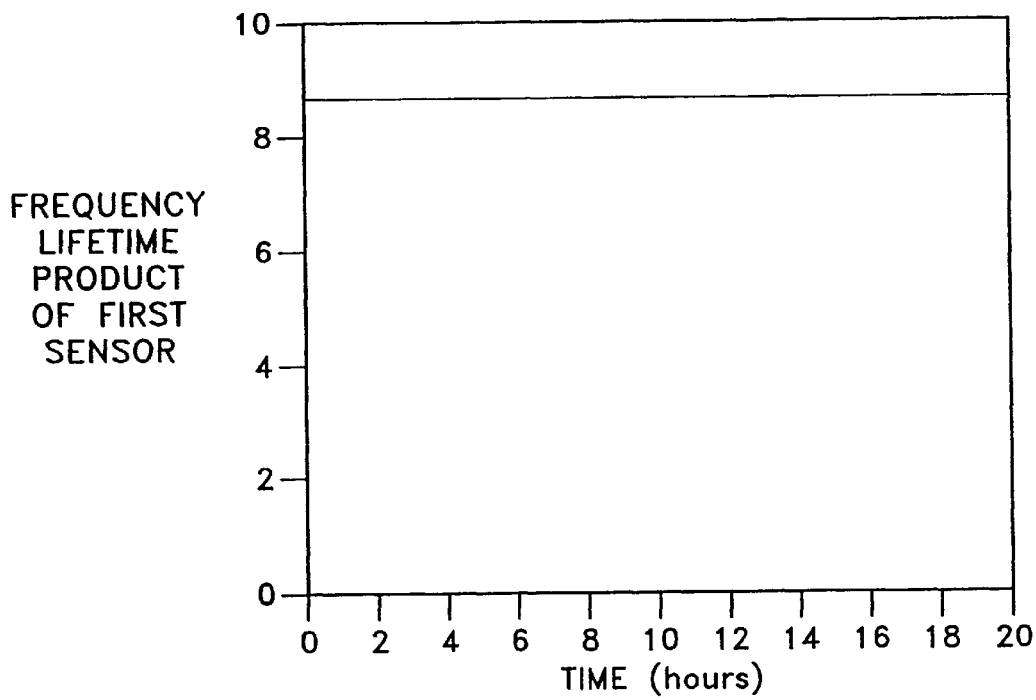
FIG. 8 is a plot showing frequency lifetime product, $\omega\tau$, versus time for the first sensor material in an anaerobic vial.
Figure 9:
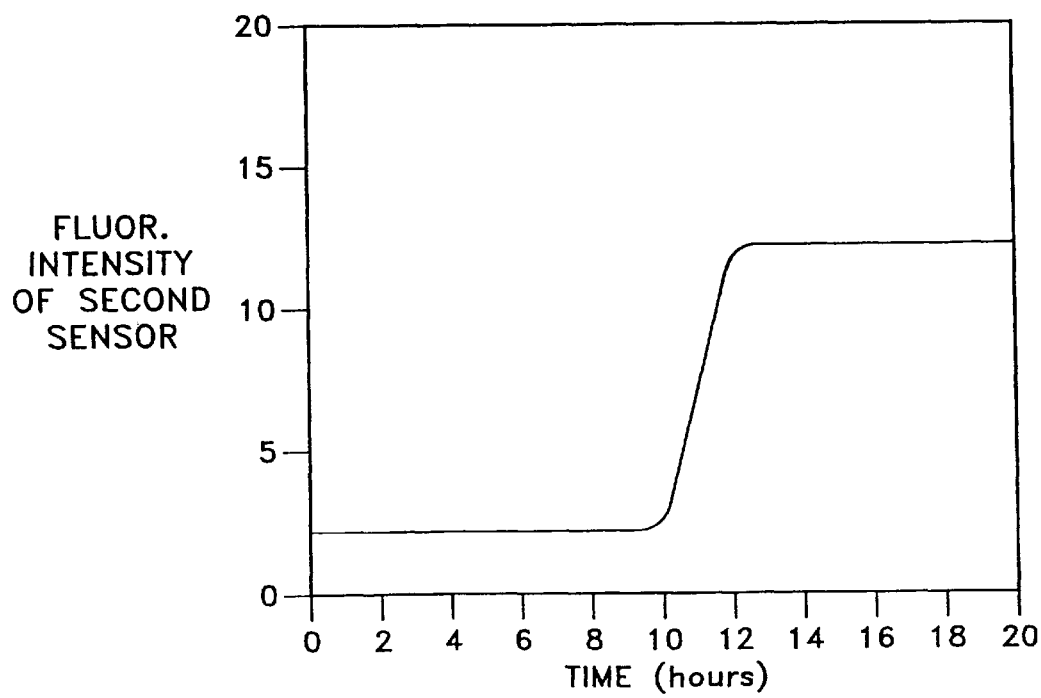
FIG. 9 is a plot showing fluorescence intensity versus time for the second sensor material for a strong carbon dioxide producing microorganism.
Figure 10:
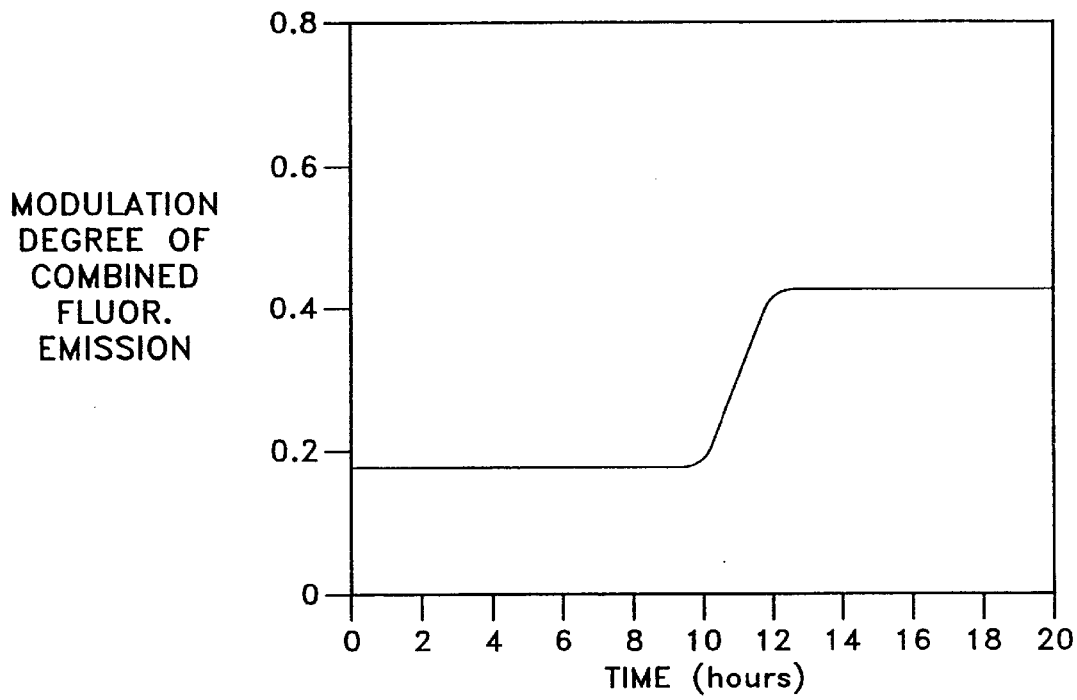
FIG. 10 is a plot showing modulation degree, AC/DC, of the combined fluorescence emission versus time, based on the individual sensor signals shown in FIGS. 8 and 9.

FIG. 4 shows the modulation degree of the combined fluorescence emissions, which is calculated within computer 11, and which represents the sensor output signal. In this case, oxygen consumption causes a decrease in the output signal. After some time delay, carbon dioxide production causes a subsequent increase in the output signal. In FIGS. 2 to 4, it has been assumed that the microorganism is a strong carbon dioxide producer. FIGS. 5 to 7 illustrate expected signals for a weak carbon dioxide producer. Finally, FIGS. 8 to 10 illustrate the expected signals for an anaerobic vial, where no oxygen changes occur during microorganism growth.

Figure 11:
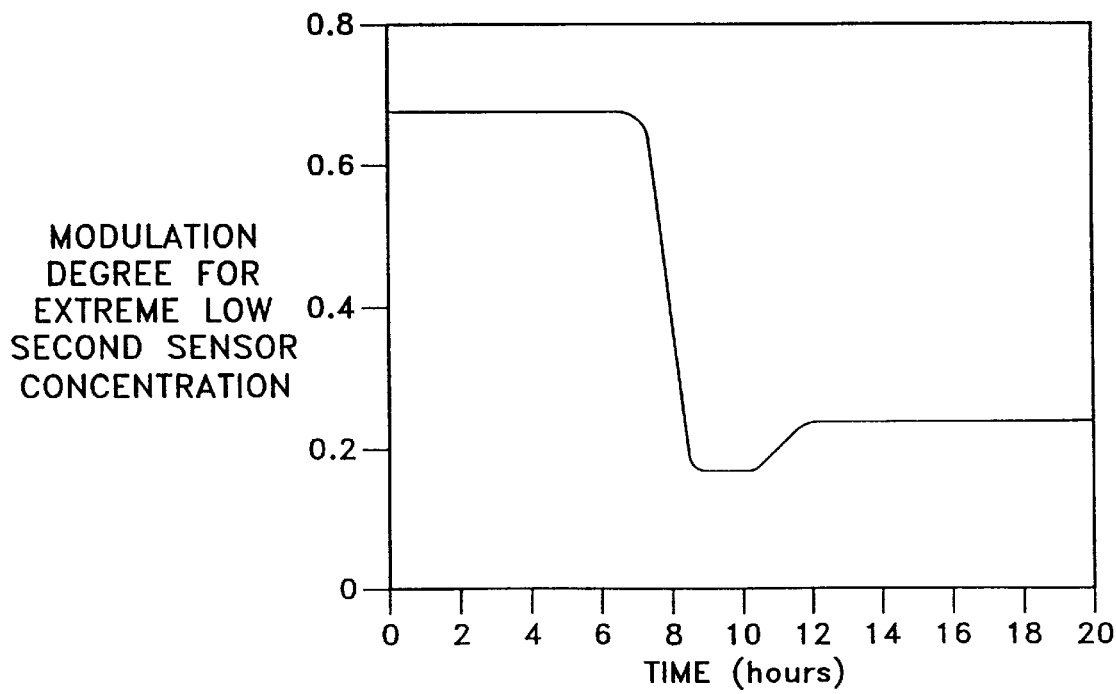
FIG. 11 is a plot showing modulation degree, AC/DC, of the combined fluorescence emission versus time, assuming an extreme low concentration for the second sensor material.
Figure 12:
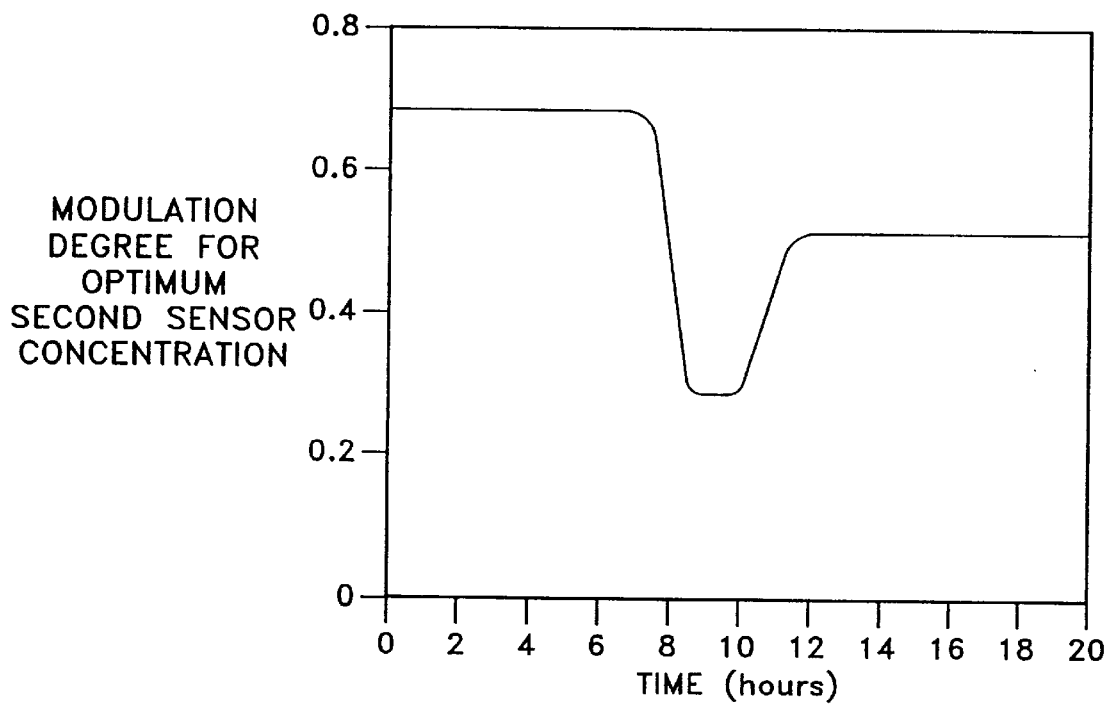
FIG. 12 is a plot showing modulation degree, AC/DC, of the combined fluorescence emission versus time, assuming an optimum concentration for the second sensor material.
Figure 13:
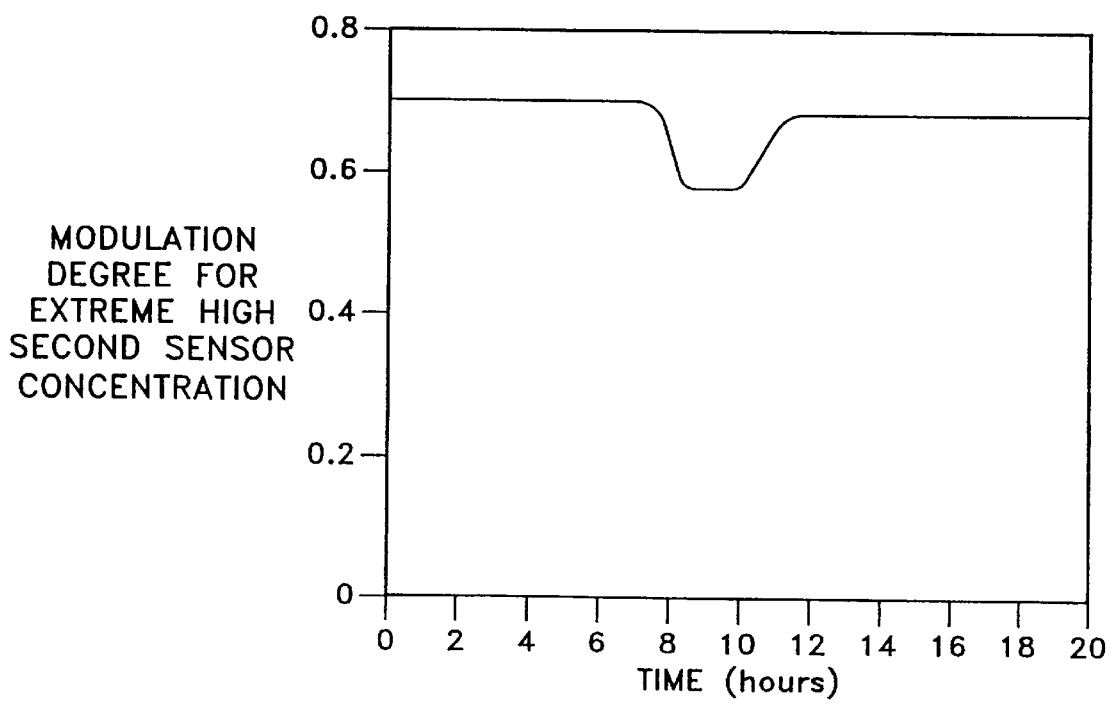
FIG. 13 is a plot showing modulation degree, AC/DC, of the combined fluorescence emission versus time, assuming an extreme high concentration for the second sensor material.

One may ask, how accurately the mixing ratio of the first sensor material and the second sensor material in mixture 3 has to be maintained during production. FIG. 11 illustrates a possible worst case scenario with an extreme low concentration of the second sensor material within the mixture 3. As can be seen, the carbon dioxide-related signal increase is much weaker than the oxygen-related signal decrease. FIG. 12 shows the sensor behavior for optimum second sensor material concentration. Here, both the oxygen-related decrease and the carbon dioxide-related increase are pronounced. FIG. 13 illustrates another possible worst case scenario with an extreme high concentration of the second sensor material within the mixture, in which the oxygen-related decrease and the carbon dioxide-related increase are weak.

Figure 14:
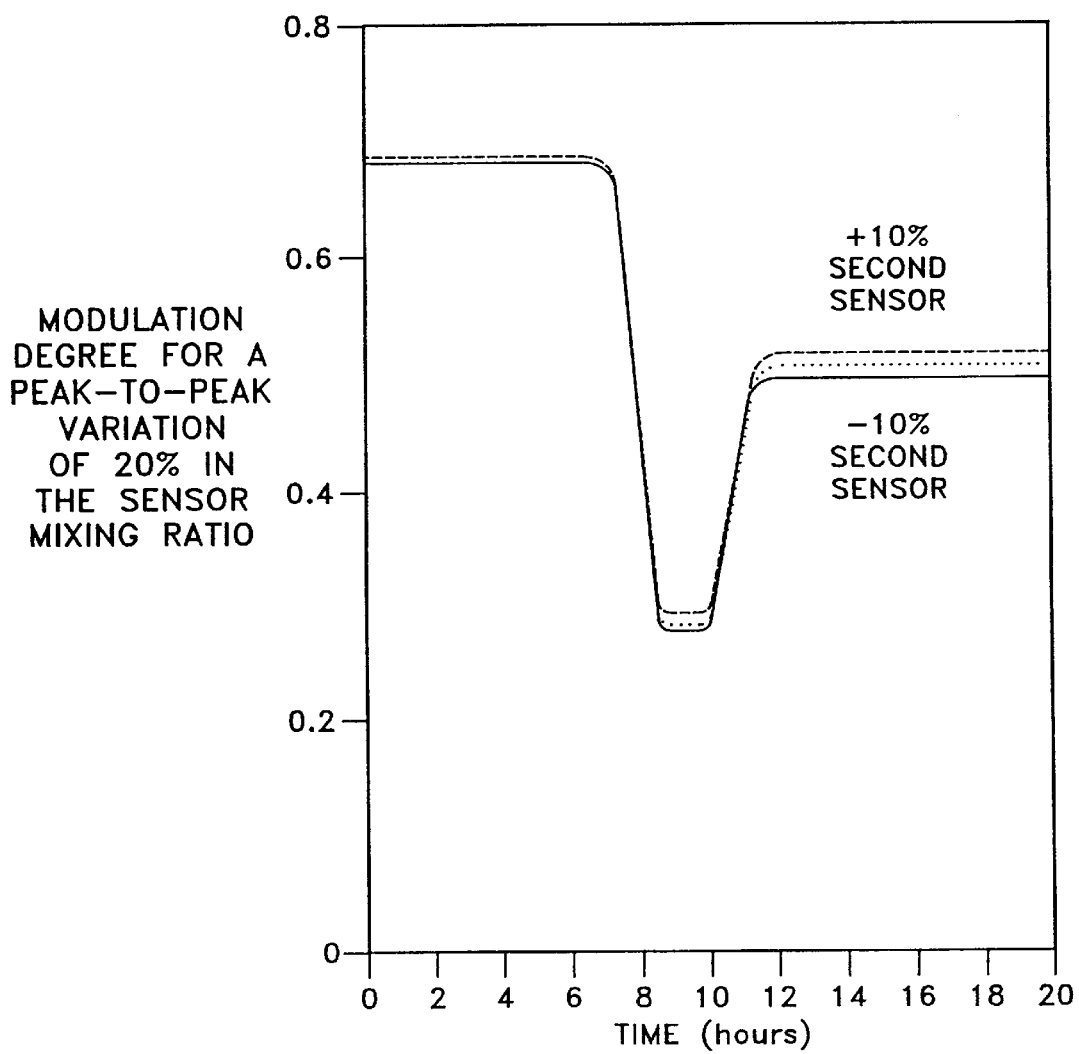
FIG. 14 is a plot showing the effect on microorganism growth curves caused by a 20 percent peak-to-peak variation in the second sensor material concentration.
Figure 15:
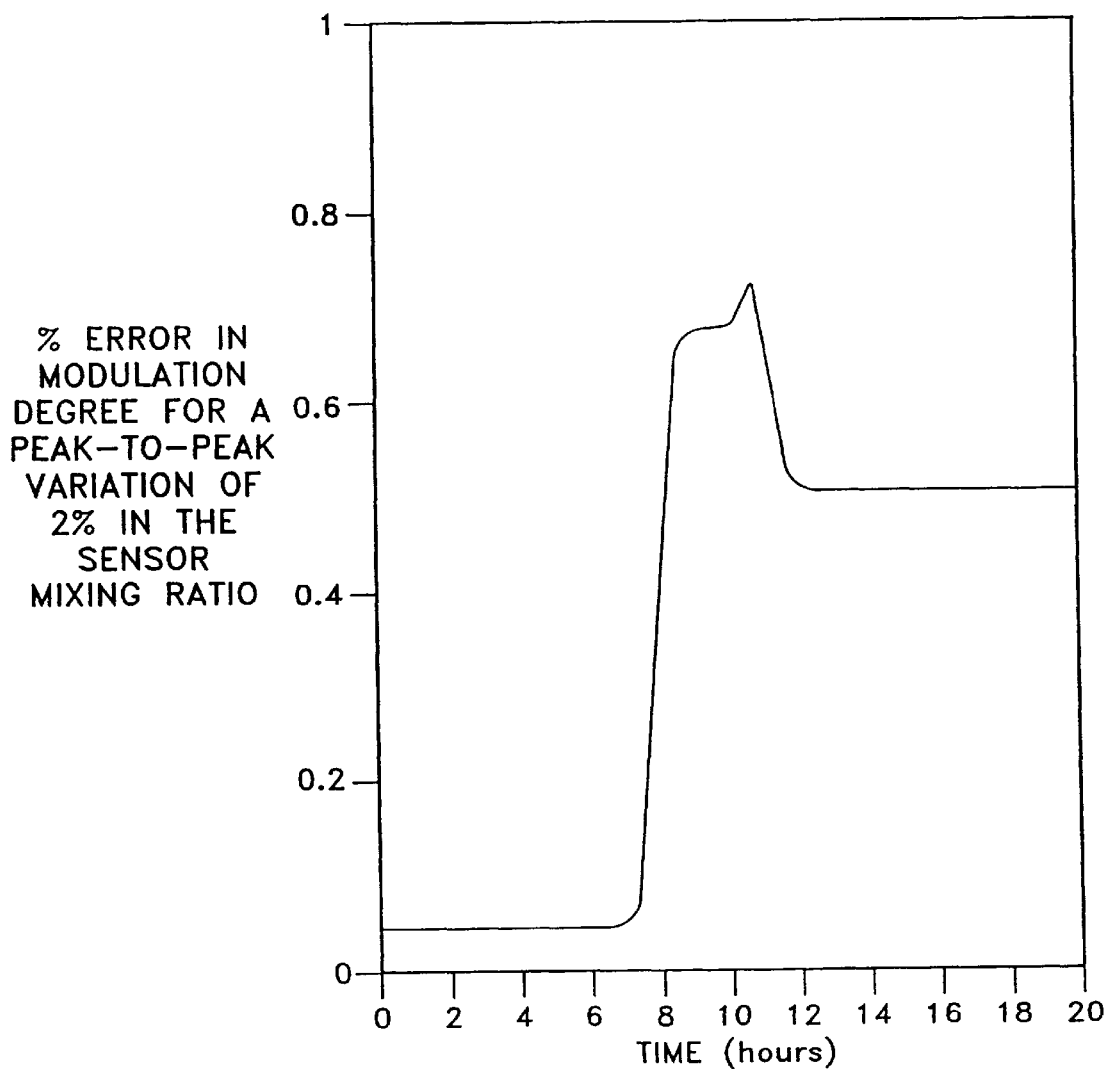
FIG. 15 is a plot showing relative error of measured modulation degree, AC/DC, in percent, assuming a 20 percent peak-to-peak variation in the second sensor material concentration.

The influence of production-related deviations in the sensor mixing ratio from the optimum mixing ratio is illustrated in FIGS. 14 and 15. FIG. 14 shows how growth curves would be affected by a 20-% peak-to-peak variation in the second sensor material concentration. FIG. 15 shows the relative error in the measured modulation degree in percent, again for a 20-% peak-to-peak variation in the second sensor material concentration. In practice, the mixing ratio can be controlled easily with an accuracy of better than 1%. In other words, the expected impact of production-related variations in the mixing ratio on the measured growth curves is well below 1%.

The expected growth curves shown in FIGS. 4, 7 and 10–14 are based on the assumption that the average fluorescence intensity of the second sensor material, $F_{02}(t)$, will increase as a consequence of carbon dioxide production during microorganism growth. This results in a different polarity for sensor output signal changes in response to oxygen consumption and carbon dioxide production, respectively. While this may be of advantage sometimes, it could result in a partial signal cancellation, if oxygen consumption and carbon dioxide production occur simultaneously.

Figure 17:
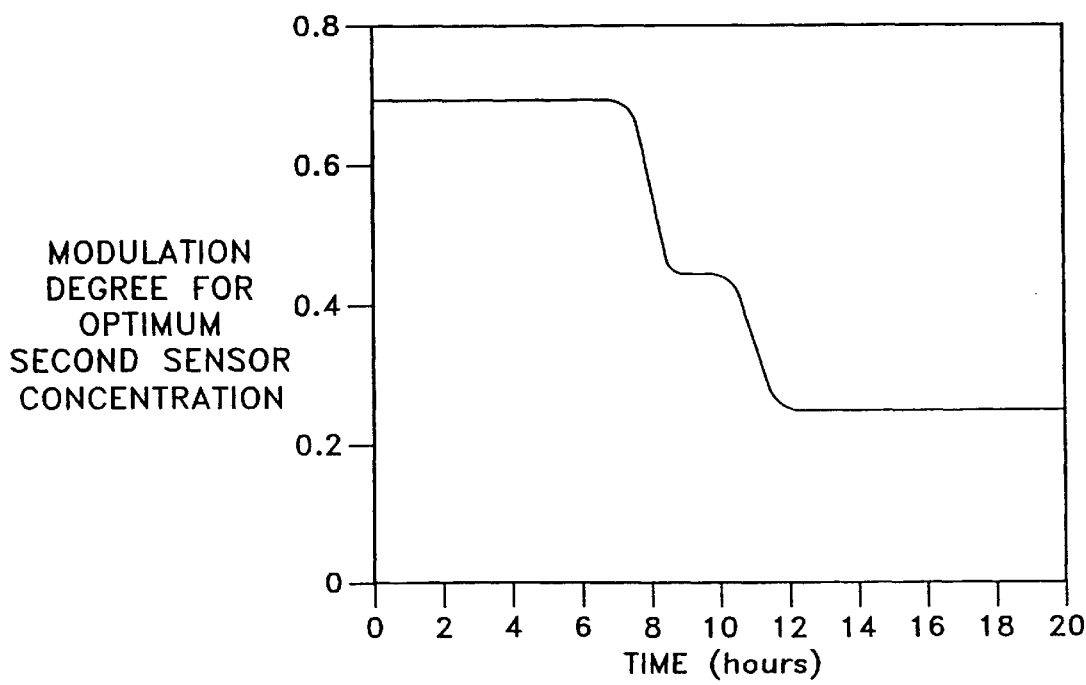
FIG. 17 is a plot showing modulation degree, AC/DC, of the combined fluorescence emission versus time, assuming an optimum concentration for a second sensor material with decreasing fluorescence intensity in response to carbon dioxide production.

Any signal cancellation can be avoided by selecting a second sensor material that shows a decrease in intensity in response to carbon dioxide production. In this case, the expected growth curve shown in FIG. 4 changes to a growth curve as depicted in FIG. 17. Therefore, both oxygen consumption and carbon dioxide production cause a decrease in the modulation degree, i.e., generate sensor output signal changes that have the same polarity.

Figure 16:
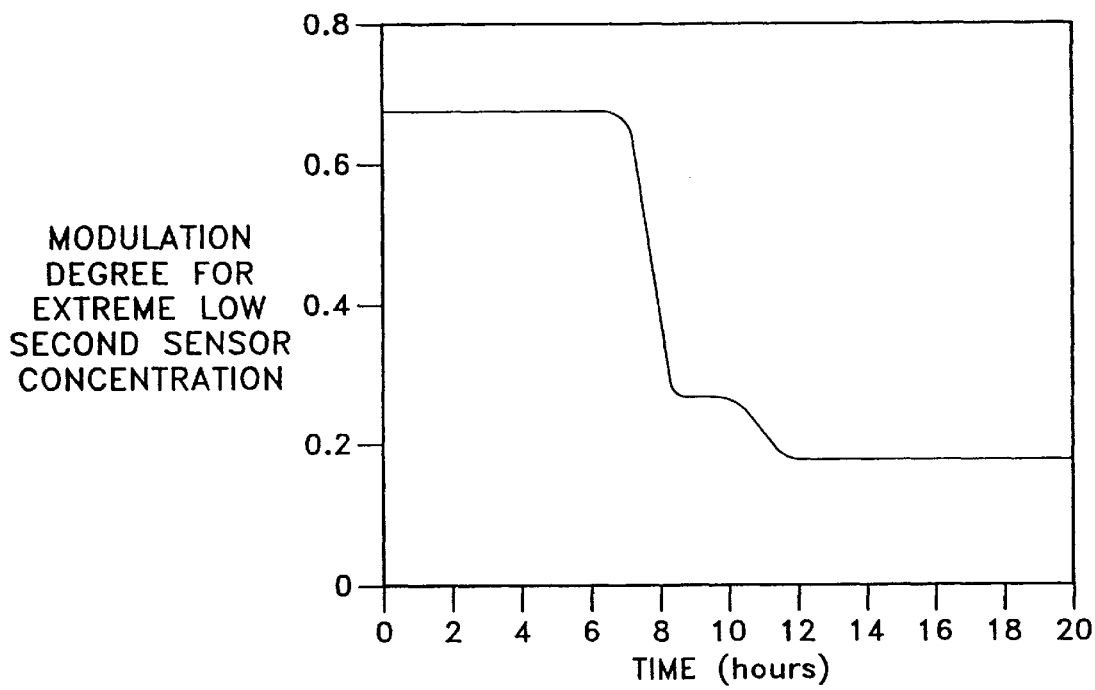
FIG. 16 is a plot showing modulation degree, AC/DC, of the combined fluorescence emission versus time, assuming an extreme low concentration for a second sensor material with a decreasing fluorescence intensity in response to carbon dioxide production.
Figure 18:
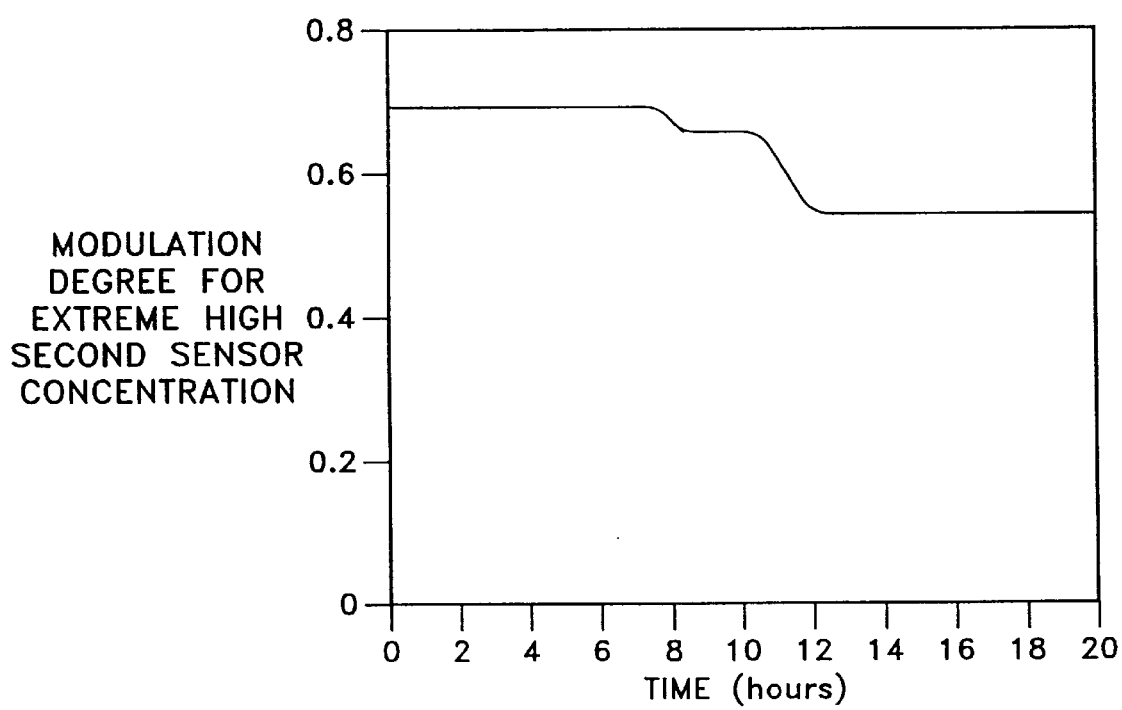
FIG. 18 is a plot showing modulation degree, AC/DC, of the combined fluorescence emission versus time, assuming an extreme high concentration for a second sensor material with a decreasing fluorescence intensity in response to carbon dioxide production.
Figure 19:
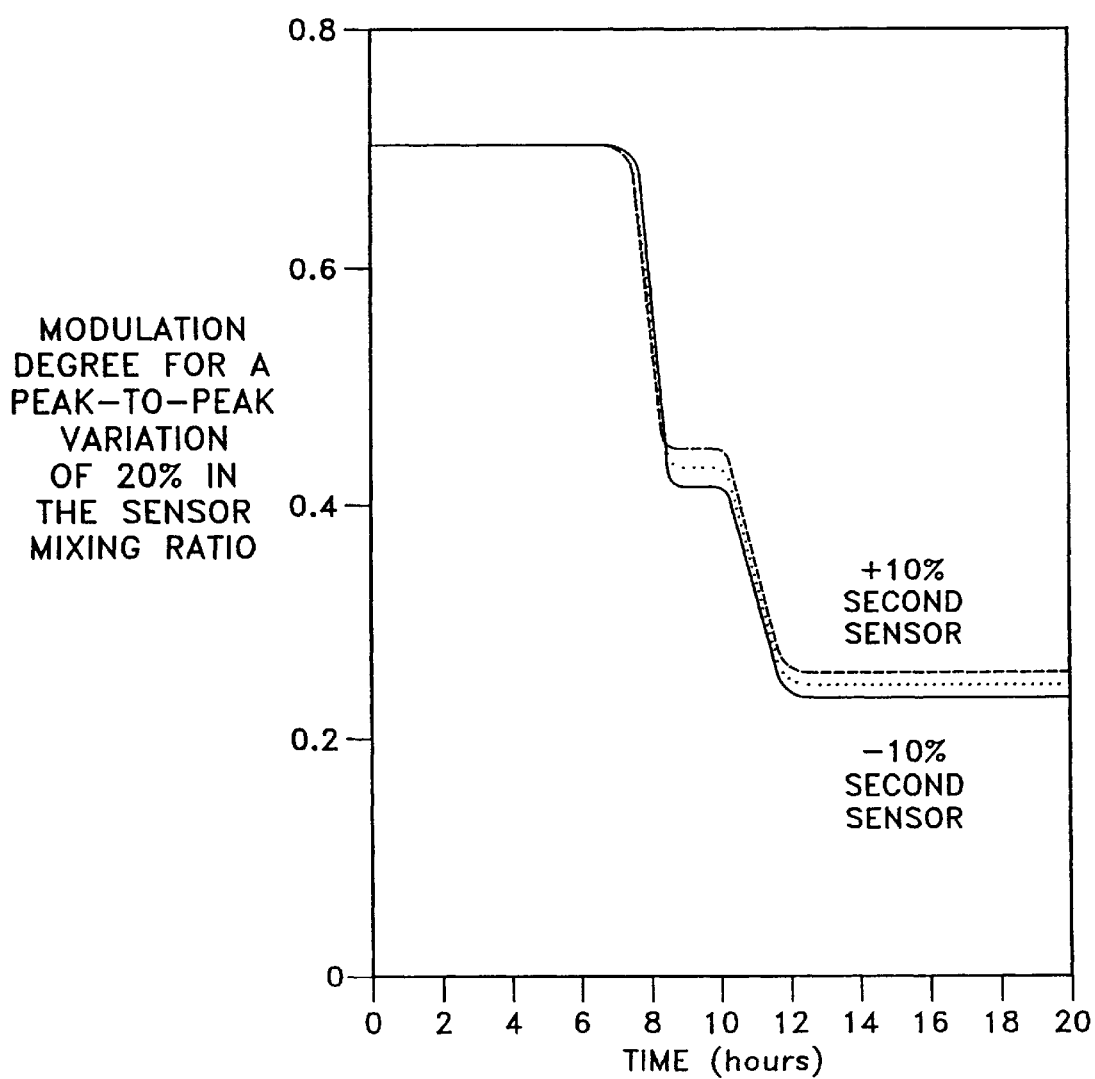
FIG. 19 is a plot showing the effect on microorganism growth curves caused by a 20 present peak-to-peak variation in the second sensor material concentration, assuming a second sensor material with a decreasing fluorescence intensity in response to carbon dioxide production.
Figure 20:
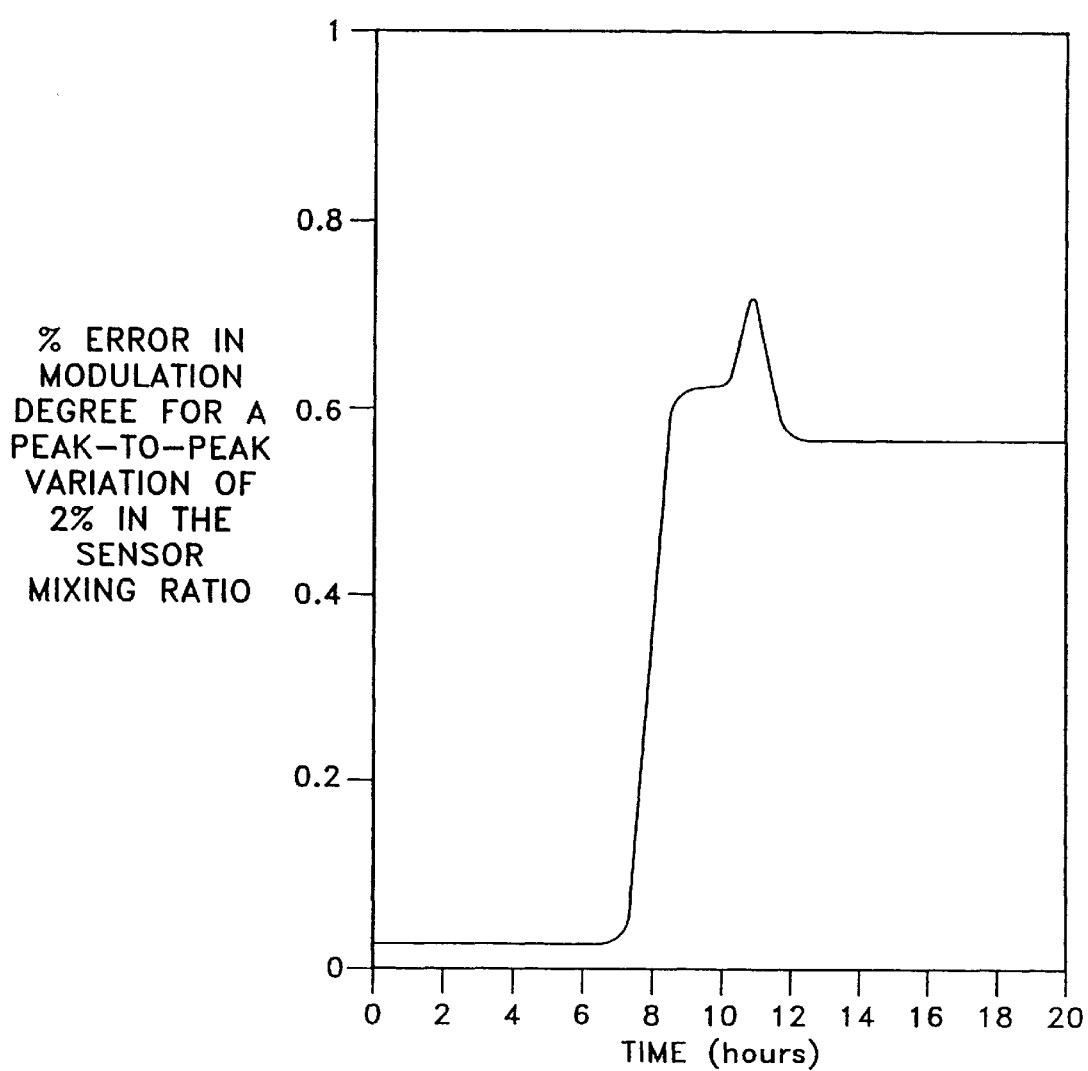
FIG. 20 is a plot showing relative error of measured modulation degree, AC/DC, in percent, assuming a 20 percent peak-to-peak variation in a second sensor material concentration, and assuming a second sensor material with a decreasing fluorescence intensity in response to carbon dioxide production.
Figure 21A:
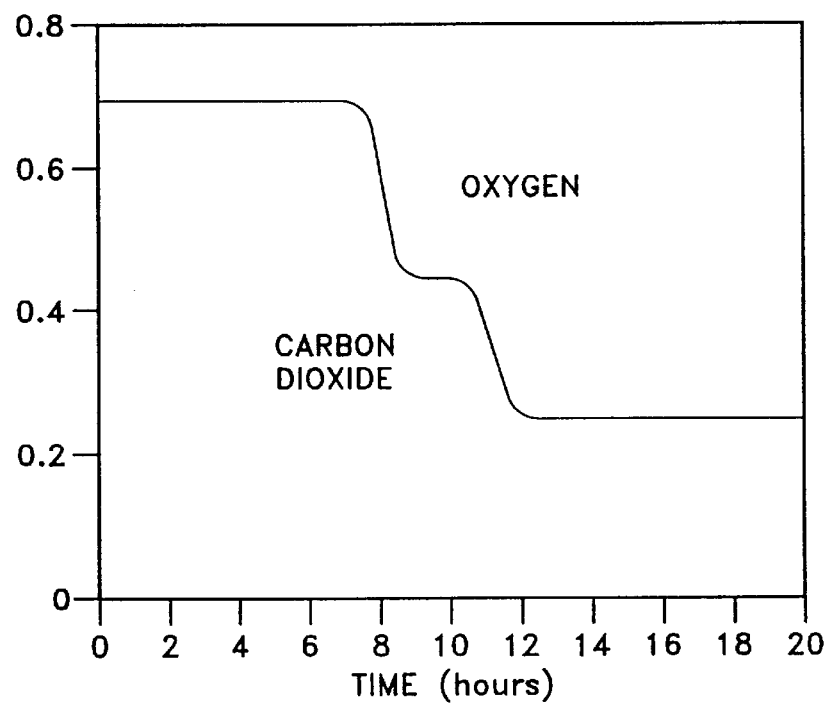
FIGS. 21a–21d illustrate two growth curves and their first derivatives for aerobic sample vials with the curves on the left corresponding to a strong carbon dioxide producer and the curves on the right to a weak one.
Figure 21B:
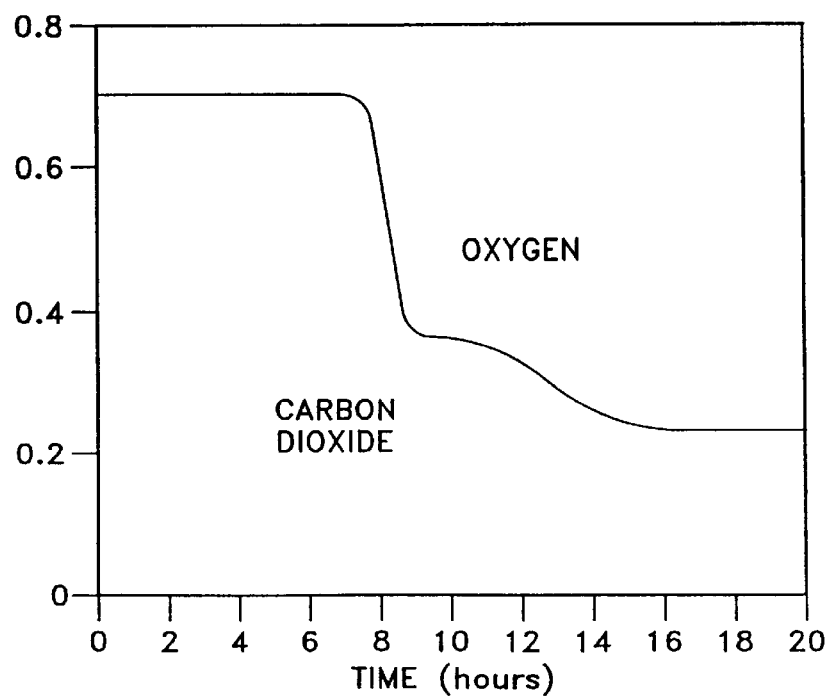
Figure 21C:
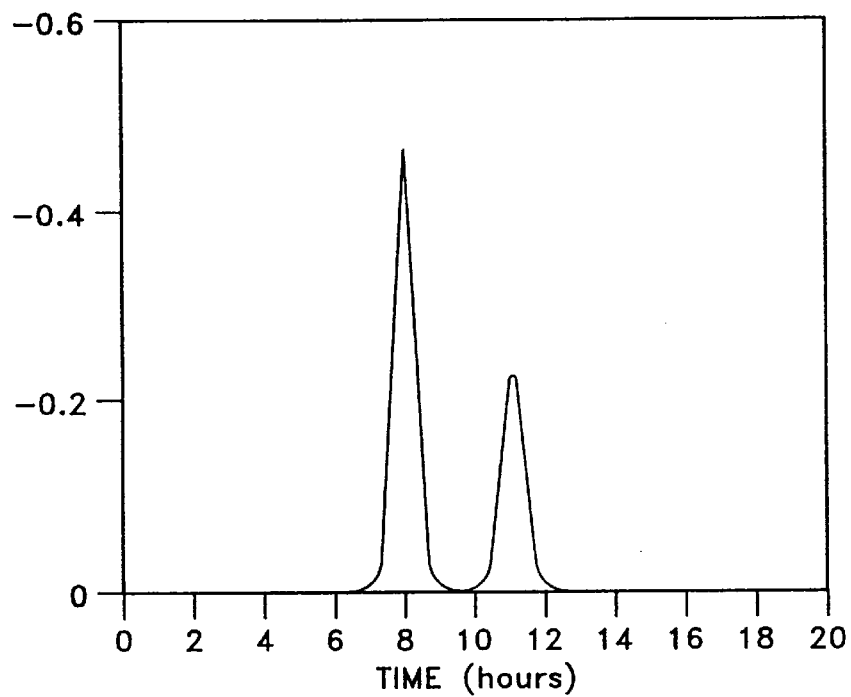
Figure 21D:
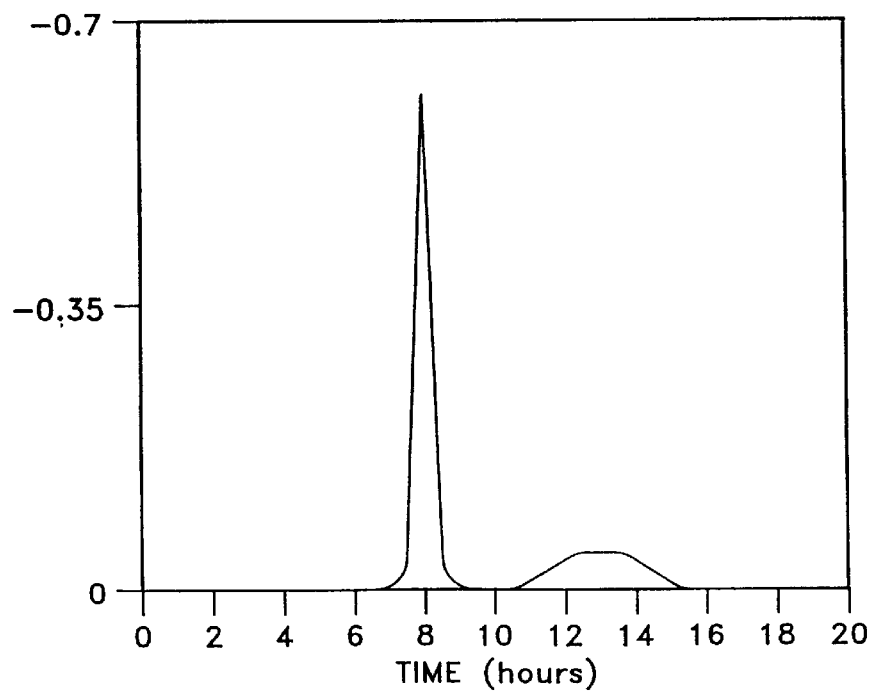

The plots depicted in FIGS. 16, 17, and 18 correspond to the plots shown in FIGS. 11, 12 and 13 and illustrate the effect of a varying mixing ratio for the two sensor materials for the case where the second sensor material exhibits a decreasing fluorescence intensity. FIGS. 19 and 20 correspond to FIGS. 14 and 15, respectively, and illustrate how growth curves would be affected by a 20-% peak-to-peak variation in the second sensor material concentration. The conclusions are the same as in the case of a second sensor material showing an increasing fluorescence intensity.

Figure 22:
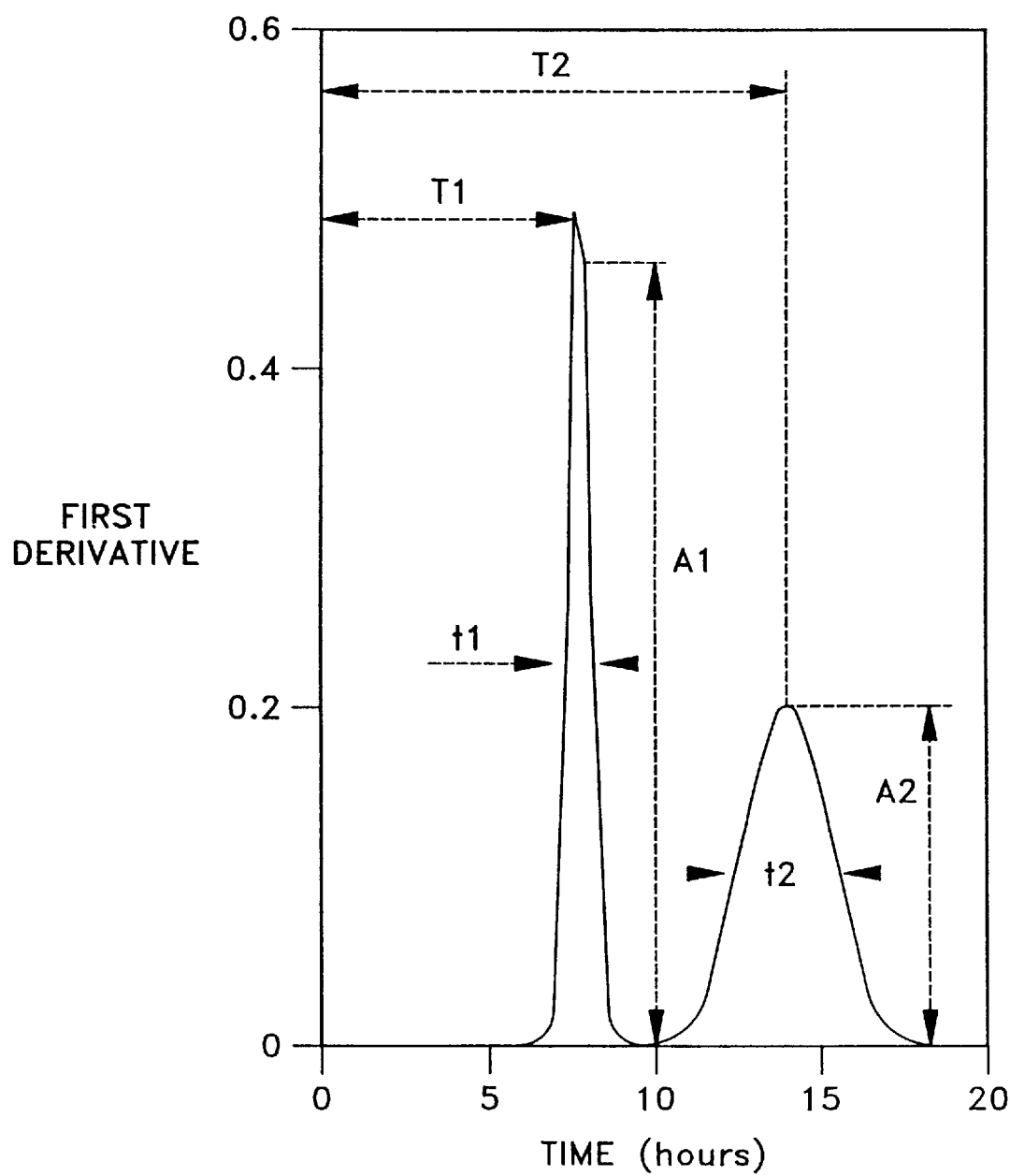
FIG. 22 depicts possible parameters of the first derivative plots that could be extracted as features in order to execute identification algorithms.

FIG. 21 illustrates two growth curves for aerobic sample vials. The curve on the left corresponds to a strong carbon dioxide producer; the curve on the right to a weak one. FIG. 21 also contains the first derivatives of the growth curves. As can be seen, different organisms may produce different patterns that can be utilized to perform presumptive microorganism identifcation. FIG. 22 depicts possible parameters of the first derivative plots that could be extracted as features in order to execute identification algorithms.

As described above, the fluorescence analysis can be performed by measuring the AC and DC components of the photocurrent, and by calculating the AC/DC ratio, which corresponds to the fluorescence modulation degree. It is also possible to apply other methods of time-resolved fluorescence analysis.

A further modification of the present invention is possible by measuring the fluorescence modulation using a first modulation frequency, repeating the same procedure and applying another modulation frequency, or other modulation frequencies. By analyzing the data obtained at different frequencies, changes in the first and second chemical parameters can be isolated, even if these changes would occur simultaneously. Separating the effects of changes in the first and second chemical parameter allows for microorganism identification, because different species will generate different time patterns in regard to the two chemical parameters.

In summary, an optical blood culture sensor according to the present invention cancels out the effects of variations in excitation source intensity, photodetector sensitivity, optical filter transmission, and vial shape. Moreover, the requirements in maintaining a constant mixing ratio for the two sensors are very modest.

It should be understood that the above-described embodiments are simply illustrative of an apparatus and method embodying the principles and concepts of the present invention. Of course, other suitable variations and modifications could also be made to the apparatus and method described and still remain within the scope of the present invention.

What is claimed is:

1. An apparatus for detecting microorganism growth comprising:

a container comprising a culture medium, a blood specimen, and a head space having a concentration of a gas;

a chemically sensitive composite material in said container for detecting microorganism growth within said container when illuminated with an intensity-modulated light, said chemically sensitive composite material being comprised of a first fluorescent material and a second fluorescent material;

said first fluorescent material exhibiting a fluorescence decay time that depends on a first chemical parameter of said gas;

said second fluorescent material exhibiting a fluorescence intensity that depends on a second chemical parameter of said gas and having a fluorescence decay time at least one order of magnitude shorter than the fluorescence decay time of said first fluorescent material;

means for generating said intensity-modulated light using a single excitation source;

means for detecting and analyzing a fluorescence emitted from said chemically sensitive composite material, wherein said means for detecting and analyzing include a single emission filter and a single photodetector and said first and second fluorescent materials have the same absorption spectrum and emission spectrum; and means for determining whether microorganism growth is occurring in said container based on changes in the analyzed fluorescence in response to changes in the first and second chemical parameters.

2. An apparatus according to claim 1, wherein said first chemical parameter of said gas is oxygen concentration and said second chemical parameter of said gas is carbon dioxide concentration.

3. An apparatus according to claim 1, wherein said intensity-modulated light is periodically modulated.

4. An apparatus according to claim 1, wherein said intensity-modulated light is sinusoidally modulated.

5. An apparatus according to claim 1, wherein said intensity-modulated light is square-wave modulated.

6. An apparatus according to claim 1, wherein said intensity-modulated light is periodically pulsed.

7. An apparatus according to claim 1, wherein said first fluorescent material has a fluorescence decay time in the range 0.1 to 1000 $\mu$sec.

8. An apparatus according to claim 1, wherein said first fluorescent material has a fluorescence decay time in the range 1 to 100 nsec.

9. An apparatus according to claim 1, wherein said means for detecting and analyzing the fluorescence emitted from said chemically sensitive composite material performs a time-resolved fluorescence analysis.

10. An apparatus according to claim 1, wherein a time-resolved fluorescence analysis is performed at more than one modulation frequency.

11. An apparatus according to claim 1, wherein a microorganism identification is performed based on analyzing changes in the first and second chemical parameters.

12. An apparatus for detecting microorganism growth comprising:

a container comprising a culture medium, a blood specimen, and a head space having a concentration of a gas;

a chemically sensitive composite material in said container for detecting microorganism growth within said container when illuminated with an intensity-modulated light, said chemically sensitive composite material being comprised of a first fluorescent material and a second fluorescent material;

said first fluorescent material exhibiting a fluorescence intensity that depends on a first chemical parameter of said gas;

said second fluorescent material exhibiting a fluorescence intensity that depends on a second chemical parameter of said gas and having a fluorescence decay time at least one order of magnitude shorter than the fluorescence decay time of said first fluorescent material;

means for generating said intensity-modulated light using a single excitation source;

means for detecting and analyzing a fluorescence emitted from said chemically sensitive composite material wherein said means for detecting and analyzing include a single emission filter and a single photodetector and said first and second fluorescent materials have the same absorption spectrum and emission spectrum; and means for determining whether microorganism growth is occurring in said container based on changes in the analyzed fluorescence in response to changes in the first and second chemical parameters.

13. An apparatus according to claim 12, wherein said first chemical parameter of said gas is oxygen concentration and said second chemical parameter of said gas is carbon dioxide concentration.

14. An apparatus according to claim 12, wherein said intensity-modulated light is periodically modulated.

15. An apparatus according to claim 12, wherein said intensity-modulated light is sinusoidally modulated.

16. An apparatus according to claim 12, wherein said intensity-modulated light is square-wave modulated.

17. An apparatus according to claim 12, wherein said intensity-modulated light is periodically pulsed.

18. An apparatus according to claim 12, wherein said first fluorescent material has a fluorescence decay time in the range 0.1 to 1000 $\mu$sec.

19. An apparatus according to claim 12, wherein said first fluorescent material has a fluorescence decay time in the range 1 to 100 nsec.

20. An apparatus according to claim 12, wherein said means for detecting and analyzing the fluorescence emitted from said chemically sensitive composite material performs a time-resolved fluorescence analysis.

21. An apparatus according to claim 12, wherein a time-resolved fluorescence analysis is performed at more than one modulation frequency.

22. An apparatus according to claim 12, wherein a microorganism identification is performed based on analyzing changes in the first and second chemical parameters.

23. A method for detecting microorganism growth comprising the steps of:

forming a chemically sensitive composite material of a first fluorescent material and a second fluorescent material;

mounting the chemically sensitive composite material in a container for detecting microorganism growth within the container when illuminated with an intensity-modulated light;

introducing a culture medium and a blood specimen into the container and forming a head space in the container having a concentration of a gas;

illuminating the chemically sensitive composite material in the container with an intensity-modulated light, whereby the first fluorescent material exhibits a fluorescence decay time depending on a first chemical parameter of the gas and the second fluorescent material exhibits a fluorescence intensity depending on a second chemical parameter of the gas and has a fluorescence decay time at least one order of magnitude shorter than the fluorescence decay time of the first fluorescent material and said first and second fluorescent materials have the same absorption spectrum and emission spectrum;

generating said intensity-modulated light using a single excitation source;

detecting and analyzing a fluorescence emitted from the chemically sensitive composite material using a single emission filter and a single photodetector; and determining whether microorganism growth is occurring in the container based on changes in the analyzed fluorescence in response to changes in the first and second chemical parameters.

24. A method according to claim 23, wherein the first chemical parameter of the gas is oxygen concentration and the second chemical parameter of the gas is carbon dioxide concentration.

25. A method according to claim 23, wherein the intensity-modulated light is periodically modulated.

26. A method according to claim 23, wherein the intensity-modulated light is sinusoidally modulated.

27. A method according to claim 23, wherein the intensity-modulated light is square-wave modulated.

28. A method according to claim 23, wherein the intensity-modulated light is periodically pulsed.

29. A method according to claim 23, wherein the first fluorescent material has a fluorescence decay time in the range 0.1 to 1000 $\mu$sec.

30. A method according to claim 23, wherein the first fluorescent material has a fluorescence decay time in the range 1 to 100 nsec.

31. A method according to claim 23, wherein said step of detecting and analyzing the fluorescence emitted from said chemically sensitive composite material performs a time-resolved fluorescence analysis.

32. A method according to claim 23, wherein a time-resolved fluorescence analysis is performed at more than one modulation frequency.

33. A method according to claim 23, wherein a microorganism identification is performed based on analyzing changes in the first and second chemical parameters.

34. A method for detecting microorganism growth comprising the steps of:

forming a chemically sensitive composite material of a first fluorescent material and a second fluorescent material;

mounting the chemically sensitive composite material in a container for detecting microorganism growth within the container when illuminated with an intensity-modulated light;

introducing a culture medium and a blood specimen into the container and forming a head space in the container having a concentration of a gas;

illuminating the chemically sensitive composite material in the container with an intensity-modulated light, whereby the first fluorescent material exhibits a fluorescence intensity depending on a first chemical parameter of the gas and the second fluorescent material exhibits a fluorescence intensity depending on a second chemical parameter of the gas and has a fluorescence decay time at least one order of magnitude shorter than the fluorescence decay time of the first fluorescent material and said first and second fluorescent materials have the same absorption spectrum and emission spectrum;

generating said intensity-modulated light using a single excitation source;

detecting and analyzing a fluorescence emitted from the chemically sensitive composite material using a single emission filter and a single photodetector; and determining whether microorganism growth is occurring in the container based on changes in the analyzed fluorescence in response to changes in the first and second chemical parameters.

35. A method according to claim 34, wherein the first chemical parameter of the gas is oxygen concentration and the second chemical parameter of the gas is carbon dioxide concentration.

36. A method according to claim 34, wherein the intensity-modulated light is periodically modulated.

37. A method according to claim 34, wherein the intensity-modulated light is sinusoidally modulated.

38. A method according to claim 34, wherein the intensity-modulated light is square-wave modulated.

39. A method according to claim 34, wherein the intensity-modulated light is periodically pulsed.

40. A method according to claim 34, wherein the first fluorescent material has a fluorescence decay time in the range 0.1 to 1000 $\mu$sec.

41. A method according to claim 34, wherein the first fluorescent material has a fluorescence decay time in the range 1 to 100 nsec.

42. A method according to claim 34, wherein said step of detecting and analyzing the fluorescence emitted from said chemically sensitive composite material performs a time-resolved fluorescence analysis.

43. A method according to claim 34, wherein a time-resolved fluorescence analysis is performed at more than one modulation frequency.

44. A method according to claim 34, wherein a microorganism identification is performed based on analyzing changes in the first and second chemical parameters.

* * * * *